United States Patent [19]

Block

[11] Patent Number: 5,525,324
[45] Date of Patent: Jun. 11, 1996

[54] ORGANIC SILICON CONTRAST AGENTS AND METHODS OF USE

[76] Inventor: Ronald E. Block, 545 NE. 112 St., Miami, Fla. 33161

[21] Appl. No.: 102,947

[22] Filed: Aug. 6, 1993

[51] Int. Cl.$^6$ .................................................. A61B 5/055
[52] U.S. Cl. ................ 424/9.3; 436/173; 514/63
[58] Field of Search ............. 424/9, 9.3; 436/173; 128/653.4, 654; 514/63

[56] References Cited

U.S. PATENT DOCUMENTS

| | | | |
|---|---|---|---|
| 4,804,529 | 2/1989 | Bardy et al. | 424/9 |
| 4,951,675 | 8/1990 | Groman et al. | 128/653.4 |
| 5,171,755 | 12/1992 | Kaufman et al. | 514/749 |

FOREIGN PATENT DOCUMENTS

91/14457  10/1991  WIPO .

*Primary Examiner*—Gary E. Hollinden
*Attorney, Agent, or Firm*—Dressler, Goldsmith, Shore & Milnamow, Ltd.

[57] ABSTRACT

This invention is directed to a magnetic resonance imaging composition for imaging of an organ or organ system comprising an organic silicon compound. Preferably, the organ system is the gastrointestinal tract. The present invention is further directed to a method of diagnosis comprising administering to a mammal a contrast effective amount of an organic silicon compound suspended or dispersed in a physiologically tolerable carrier and generating a magnetic resonance image of said mammal. In a preferred embodiment, the organic silicon compound is a silane. In another preferred embodiment, the organic silicon compound is a siloxane. In yet another preferred embodiment, the organic silicon compound is a polysiloxane.

9 Claims, 2 Drawing Sheets

ORGANIC SILICON CONTRAST AGENTS AND METHODS OF USE

FIELD OF THE INVENTION

This invention relates to compositions useful in magnetic resonance imaging. More particularly, this invention relates to organic silicon containing compositions that can be used in magnetic resonance imaging of organs.

BACKGROUND OF THE INVENTION

Magnetic resonance imaging systems rely on the tendency of atomic nuclei possessing magnetic moments to align their spins with an external magnetic field. Because only nuclei with odd numbers of nucleons have a magnetic moment, only those nuclei can be detected and imaged using magnetic resonance. At present, hydrogen with one nucleon, a proton, in its nucleus is the element of choice for diagnostic tissue imaging.

The intensity of the magnetic resonance (MR) image depends upon the nuclear spin relaxation parameters denoted $T_1$ and $T_2$ in the region being imaged. $T_1$ is the rate constant for signal recovery after the nuclear spins have been inverted by a radiofrequency pulse. $T_1$ is called the spin lattice relaxation time.

$T_2$ depends upon the dephasing of proton spins with each other as they precess in the magnetic field. $T_2$ is called the spin-spin relaxation time.

Other factors influence the MR image. Such factors include concentration of nuclear spins, diffusion, and chemical shift.

Contrast media also have an influence on the MR image. Paramagnetic metals have been traditionally used as contrast media, but are not universally useful, and are costly. Other contrast agents useful in MR imaging of the gastrointestinal tract include superparamagnetic particles, clay minerals and perfluoro compounds.

A problem with these contrast agents is their inability to be used in certain MR imaging techniques such as lipid-suppressed $T_2$ imaging. Lipid-suppressed $T_2$ imaging involves the use of lipid signal suppression combined with a long $T_2$ weighting in the same pulse sequence. Under such conditions, a compound with one or more strong and narrow proton nuclear magnetic resonance signals can be observed, provided that the $T_2$ values of the nuclei giving rise to the lines are sufficiently long, and the chemical shift of the line(s) is significantly different from that of the lipid methylene protons in fat.

It would therefore be useful to have a contrast agent that is inexpensive and provides an image of organs and organ systems such as the gastrointestinal tract that would take advantage of the usefulness of lipid-suppressed $T_2$ weighted imaging.

BRIEF DESCRIPTION OF THE INVENTION

The present invention is directed to a magnetic resonance imaging composition for imaging of an organ or organ system comprising an organic silicon compound.

In a preferred embodiment, the organic silicon compound is a silane. A preferred silane is sodium 3-trimethylsilylpropionate- 2,2,3,3-d4.

In another preferred embodiment, the organic silicon compound is a siloxane.

In yet another preferred embodiment, the organic silicon compound is a polysiloxane. A preferred polysiloxane is a phenylmethyl polysiloxane fluid having a viscosity of about 125 centipoise at 25° C. An exemplary phenylmethyl polysiloxane is available from Dow-Corning Corporation as Dow-Corning Fluid 550.

The present invention is further directed to a method of diagnosis comprising administering to a mammal a contrast effective amount of an organic silicon compound suspended or dispersed in a physiologically tolerable carrier and generating a magnetic resonance image of said mammal. Preferably, the generating of the magnetic resonance image comprises lipid-suppressed $T_2$ weighted imaging.

In a preferred embodiment, the organic silicon compound is a silane. Preferably, the silane is sodium 3-trimethylsilylpropionate-2,2,3,3-d4.

In another preferred embodiment, the organic silicon compound is a siloxane.

In a yet further preferred embodiment, the organic silicon compound is a polysiloxane. A preferred polysiloxane is a phenylmethyl polysiloxane fluid.

DETAILED DESCRIPTION OF THE INVENTION

Figure 1:
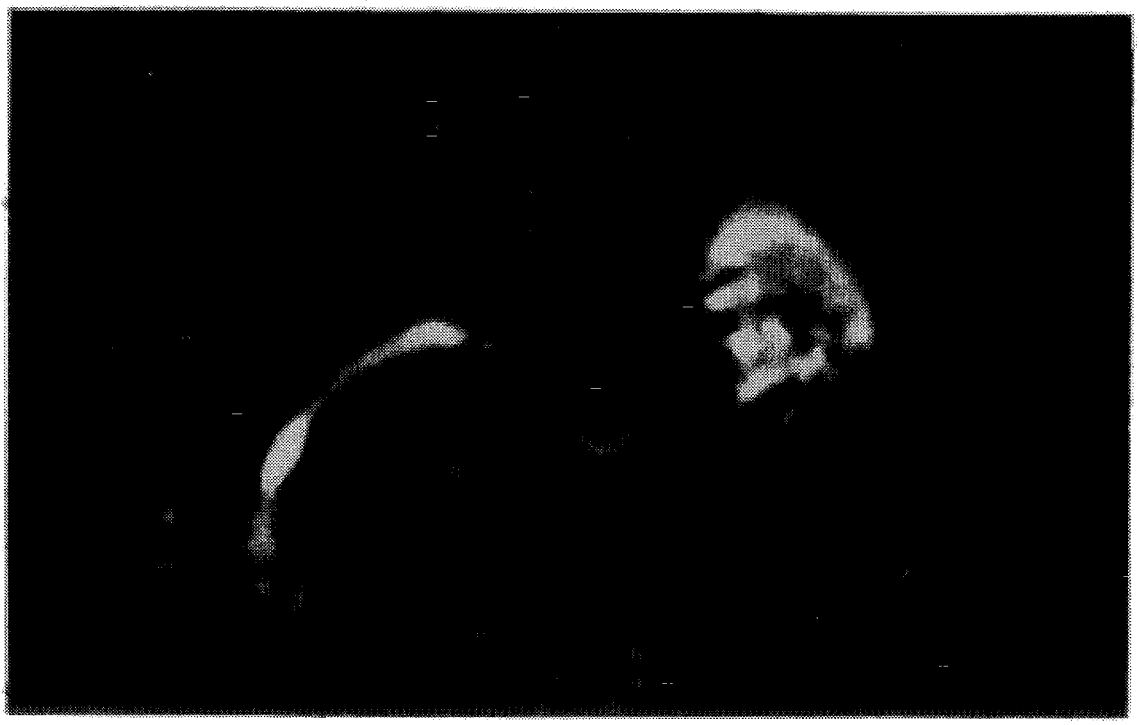
FIG. 1 shows the lipid-suppressed $T_2$ weighted MR image of a rat abdomen in the coronal plane after the animal was given 1.5 cc of Dow-Corning Fluid 550 by stomach tube (prone position, TE/TR=90/850 msec).

The present invention offers several advantages over other currently used contrast agents. Organic silicon compounds can be used under lipid-suppressed $T_2$ weighted proton imaging conditions, while other contrast agents, such as paramagnetic compounds, cannot. Using the compositions and methods of the present invention, the visibility and proximity of, for example, cancerous tissue to the organs or organ systems being imaged can be much more easily be determined.

A further advantage is that organic silicon compounds do not shorten the spin relaxation times of water in their vicinity, as do paramagnetic contrast agents. Therefore, organic silicon-containing contrast agents can be used irrespective of whether other anatomical structures are to be examined by the use of paramagnetic contrast agents by a different pulse imaging sequence. For example, the organic silicon compounds of the present invention can be administered according to the methods of the present invention to visualize the gastrointestinal tract, while paramagnetic agents can be administered intravenously to highlight a different structure in a subsequent MR imaging examination with a different MR imaging pulse sequence.

A still further advantage derives from the usefulness of the silicon-containing contrast agent of the present invention in high field strength MR imaging equipment. The trend in MR imaging equipment is to develop such equipment with higher field strength magnets. Since $T_1$ values of tissue water protons increase, and those of different tissues tend to converge, with an increase in field strength, such higher field strength MR imaging equipment will provide less contrast between tissues being imaged based on $T_1$ values. However, the contrast of the organic silicon-containing contrast agents of the present invention will improve with the use of higher field strength MR imaging equipment. This is because chemical shift selective suppression of the main fat signal from the lipid methylene protons will be improved with less effect on the methyl proton signal of silicon-containing siloxanes and polysiloxanes.

The present invention is directed to a magnetic resonance imaging composition for imaging of an organ or organ system comprising an organic silicon compound.

The organic silicon compound is visualized by imaging a particular organ or organ system with a magnetic resonance imaging system. The visualization of the organic silicon compound can be accomplished with commercially available magnetic imaging systems such as a General Electric 1.5 T Signa imaging system [$^1$H resonant frequency 63.9 megahertz (Mhz)]. Commercially available magnetic resonance imaging systems are typically characterized by the magnetic field strength used, with a field strength of 2.0 Tesla as the current maximum and 0.2 Tesla as the current minimum.

For a given field strength, each detected nucleus has a characteristic frequency. For example, at a field strength of 1.0 Tesla, the resonance frequency for hydrogen is 42.57 Mhz; for phosphorus-31 it is 17.24 Mhz; and for sodium-23 it is 11.26 Mhz.

As used herein, the phrase "organ or organ system" refers to an individual organ to be imaged, such as the brain or stomach, or organ systems, such as the gastrointestinal tract, comprised of more than one organ. For example, the gastrointestinal tract is comprised of the stomach, small intestine and large intestine or colon.

An organic silicon compound is a silicon containing chemical compound that comprises one or more organic radicals. Typical organic silicon compounds include silanes (Formula I, below) and siloxanes (Formula II, below):

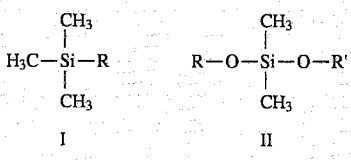

I  II

R and R' are independently $C_1$ to $C_{10}$ linear, branched or cyclic alkyl, alkenyl, alkylynyl, alkoxy, or acyl groups; or an aryl group. It is to be understood that a particular silane or siloxane can exist as a free acid or as a salt, such as, for example, 3-trimethylsilylpropionic acid or the sodium salt of 3-trimethylsilylpropionic acid.

A polysiloxane is represented by the following formula:

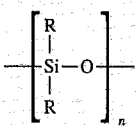

Each R is independently a $C_1$ to $C_{10}$ linear, branched or cyclic alkyl, alkenyl, alkylynyl, alkoxy, or acyl group; or an aryl group. The value n ranges from 2 to about 50 for oils.

In a preferred embodiment, the organic silicon compound is a silane. A preferred silane is sodium 3-trimethylsilylpropionate- 2,2,3,3-d4.

In another preferred embodiment, the organic silicon compound is a siloxane.

In yet another preferred embodiment, the organic silicon compound is a polysiloxane.

A preferred polysiloxane is a phenylmethyl polysiloxane fluid.

The synthesis of polysiloxanes is described in Sorenson et al., Preparative Methods of Polymer Chemistry, Interscience Publishers, Inc., New York, 1961. Briefly, the synthesis of such compounds is by hydrolysis of particular organic silicon chlorides, depending upon the particular polysiloxane to be prepared. Polysiloxanes can be linear or cyclic compounds. Low molecular weight linear polysiloxanes form the basis for so-called silicon oils.

The polysiloxanes useful in the composition and method of the present invention are those of sufficiently low molecular weight to be of an oil-like viscosity rather than a wax-like viscosity. An exemplary polysiloxane is a phenylmethyl polysiloxane fluid having a viscosity of about 125 cps at 25° C. and available commercially as Dow-Corning Fluid 550.

The present invention is further directed to a method of diagnosis comprising administering to a mammal a contrast effective amount of an organic silicon compound suspended or dispersed in a physiologically tolerable carrier and generating an NMR image of said mammal.

A contrast effective amount of an organic silicon compound is that amount necessary to provide tissue visualization with magnetic resonance imaging. Means for determining a contrast effective amount in a particular subject will depend, as is well known in the art, on the nature of the contrast agent used, the mass of the subject being imaged, the sensitivity of the magnetic resonance imaging system and the like.

After administration of the composition of the present invention, the subject mammal is maintained for a time period sufficient for the administered organic silicon compound to be distributed throughout the subject and enter the tissues of the mammal. Typically, a sufficient time period is from about 20 minutes to about 90 minutes and, preferably from about 20 minutes to about 60 minutes.

The particles are visualized by imaging that tissue with a magnetic resonance imaging system. The visualization of the particles can be accomplished with commercially available magnetic imaging systems as discussed elsewhere herein.

The present invention includes the organic silicon compounds described above formulated into compositions together with one or more non-toxic physiologically acceptable carriers, adjuvants or vehicles which are collectively referred to herein as carriers, for parenteral injection, for oral administration in solid or liquid form, for rectal or topical administration, or the like.

The compositions can be administered to humans and animals either orally, rectally, parenterally (intravenous, intramuscularly or subcutaneously), intracisternally, intravaginally, and intraperitoneally.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Preferably, the generating of the NMR comprises lipid-suppressed $T_2$ weighted imaging. Lipid-suppressed $T_2$ weighted imaging is described in Block et al., Magn. Reson. Med. 6:116–119 (1988) and Block et al., Magn. Reson. Med. 11:244–247 (1989).

Briefly, the organic silicon compound is administered as described elsewhere herein. After administration, proton imaging with a spin-echo pulse sequence is conducted, but is preceded by a chemical shift selective (CHESS) pulse at the MR frequency of the lipid methylene protons while using a TE of 72 to 95 ms. The long TE causes most water signals from normal body tissues to be suppressed while the CHESS pulse causes the main fat signal to be suppressed. This leaves the strong sharp signal from the methyl groups attache to the silicon in the organic silicon compound visible in the image.

Lipid-suppressed $T_2$ weighted imaging also leaves visible organ systems such as the central nervous system, organs such as the brain and eyes, and certain cancerous tumors, but this is not the result of the contrast agent.

It is contemplated that other fast imaging pulse sequences that suppress the imaging of most normal body tissues can be developed and used with the composition and method of the present invention.

In a preferred embodiment, the organic silicon compound is a silane. Preferably, the silane is sodium 3-trimethylsilyl-propionate-2,2,3,3-d4.

In another preferred embodiment, the organic silicon compound is a siloxane.

In a yet further preferred embodiment, the organic silicon compound is a polysiloxane.

A preferred polysiloxane is a phenylmethyl polysiloxane fluid.

The following examples further illustrate the invention and are not to be construed as limiting of the specification and claims in any way.

EXAMPLES

Experimental Methods

Adult Fischer F344 rats weighing about 180 grams were anesthetized briefly with Metofane inhalation anesthesia in order that a stomach tube could be inserted to deliver 1½ to 2 cc of the organic silicon contrast agent. The animals were then immobilized by a subcutaneous injection of Nembutal near the shoulder just prior to imaging. Various silane and siloxane compounds were investigated, including water soluble and water insoluble materials.

Images were obtained using a Bruker Biospec-II imaging and spectroscopy system operating at 4.7 Tesla with a 30 cm bore magnet. The lipid-suppressed $T_2$ weighted imaging computer program was written by adding a 2 ms Gaussian chemical shift selective pulse in a $T_2$ weighted spin-echo imaging sequence.

Animals were imaged in the prone position using 3 mm thick coronal slices with a TE of 72–90 ms and a TR of 850 ms using four acquisitions and 256 phase-encoding steps. Prior to imaging the magnet was shimmed to give a water signal linewidth from the animal of around 60 Hz. The lipid methylene proton resonance frequency was determined for each experiment in order to set the frequency of the Gaussian chemical shift selective pulse.

Results

An exemplary non-aqueous liquid comprising an organic silicon compound used for MR imaging according to the method of the present invention is Dow-Corning Fluid 550. This material was found to be brightly visible in the images of the gastrointestinal tract. However, the signal intensities of the abdominal wall muscles, fat and other structures were suppressed by the lipid-suppressed $T_2$ weighted imaging sequence. The animals survived this acute exposure, appearing robust and eating the following day.

An MR image is shown in FIG. 1, where the stomach and part of the intestinal tract can be easily located.

Figure 2:
FIG. 2 shows the lipid-suppressed $T_2$ weighted MR image of a rat abdomen in the coronal plane after the animal was given 1.5 cc of a saturated solution of 3-trimethylsilylpropionate-2,2,3,3-d4 in $D_2O$ by stomach tube.

An exemplary aqueous solution comprising an organic silicon compound is a saturated solution of sodium 3-trimethylsilylpropionate-2,2,3,3-d4 (TSP) in deuterium oxide. TSP is a water soluble chemical shift reference compound for high resolution NMR spectroscopy. TSP gave a less intense signal which was seen well distributed throughout the gastrointestinal tract (FIG. 2). Animals that had previously been fasted did not tolerate this agent well.

The foregoing specification, including the specific embodiments and examples is intended to be illustrative of the present invention and is not to be taken as limiting. Numerous other variations and modifications can be effected without departing from the true spirit and scope of the present invention.

I claim:

1. A magnetic resonance imaging composition for imaging of an organ or organ system consisting essentially of an organic silicon compound of the formula:

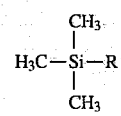

wherein R is a $C_1$ to $C_{10}$ linear, branched or cyclic alkyl, alkenyl, alkylynyl, alkoxy, or acyl group; or an aryl group.

2. A magnetic resonance imaging composition consisting essentially of an organic silicon compound of the following structure:

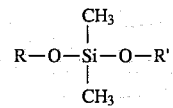

wherein R and R' are each independently a $C_1$ to a $C_{10}$ linear, branched or cyclic alkyl, alkenyl, alkylynyl, alkoxy, or acyl group; or an aryl group.

3. The composition of claim 2 wherein said compound is a phenylmethyl polysiloxane fluid having a viscosity of about 125 centipoise.

4. The composition of claim 1 wherein said compound is sodium 3-trimethylsilylpropionate-2,2,3,3-d4.

5. A method of diagnosis comprising administering to a mammal a contrast effective amount of an organic silicon compound of claim 1 suspended or dispersed in a physiologically tolerable carrier and generating a magnetic resonance image of said mammal.

6. The method of claim 5 wherein said generating of said magnetic resonance image comprises lipid-suppressed $T_2$ weighted imaging.

7. The method of claim 5 wherein said compound is sodium 3-trimethylsilylpropionate-2,2,3,3,-d4.

8. A method of diagnosis comprising administering to a mammal a contrast effective amount of an organic silicon compound of claim 2 suspended or dispersed in a physiologically tolerable carrier and generating a magnetic resonance image of said mammal.

9. The method of claim 8 wherein said organic silicon compound is a phenylmethyl polysiloxane having a viscosity of about 125 centipoise.

* * * * *